(12) United States Patent
Hirt et al.

(10) Patent No.: US 11,497,509 B2
(45) Date of Patent: Nov. 15, 2022

(54) FIXING CLAMP AND ALIGNING DEVICE

(71) Applicant: Aesculap AG, Tuttlingen (DE)

(72) Inventors: Martin Hirt, Stockach (DE); Anil Varsani, Tuttlingen/Möhringen (DE); Thomas Hermle, Rottweil (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 17/296,676

(22) PCT Filed: Nov. 28, 2019

(86) PCT No.: PCT/EP2019/082960
§ 371 (c)(1),
(2) Date: May 25, 2021

(87) PCT Pub. No.: WO2020/109499
PCT Pub. Date: Jun. 4, 2020

(65) Prior Publication Data
US 2022/0022889 A1    Jan. 27, 2022

(30) Foreign Application Priority Data
Nov. 28, 2018  (DE) ..................... 10 2018 130 117.0

(51) Int. Cl.
*A61B 17/15* (2006.01)
*A61B 17/64* (2006.01)
(52) U.S. Cl.
CPC .......... *A61B 17/157* (2013.01); *A61B 17/645* (2013.01); *A61B 17/6416* (2013.01)
(58) Field of Classification Search
CPC .................................................. A61B 17/157
See application file for complete search history.

(56) References Cited

U.S. PATENT DOCUMENTS 5,002,547 A * 3/1991 Poggie ............... A61B 17/1767
606/88
5,197,944 A * 3/1993 Steele .................. A61B 17/157
606/86 R (Continued)

FOREIGN PATENT DOCUMENTS

DE    20105643 U1    6/2001
DE    69630776        9/2004

(Continued)

OTHER PUBLICATIONS

International Search Report received in International Application No. PCT/EP2019/082960 dated Feb. 5, 2020, with translation, 5 pages.

(Continued)

*Primary Examiner* — Nicholas W Woodall
(74) *Attorney, Agent, or Firm* — Christopher A. Rothe; Culhane Meadows, PLLC

(57) ABSTRACT

A fixing clamp for an aligning device, and an aligning device that includes the fixing clamp, for clamping to a bodily extremity. The clamp includes a first clamp arm, a second clamp arm and a frame device having an attaching section for attaching to an adjustment rod. The first clamp arm is rotatably attached to a first rotary joint about a first axis of rotation, and the second clamp arm is rotatably connected to a second rotary joint about a second axis of rotation. A locking mechanism locks the first clamp arm and/or the second clamp arm relative to the frame device in at least one position, and blocks movement of the first or second clamp arm about the respective rotary joint in an open rotational direction.

23 Claims, 2 Drawing Sheets

(56) References Cited

U.S. PATENT DOCUMENTS

| | | | |
|---|---|---|---|
| 5,628,750 A * | 5/1997 | Whitlock | A61B 17/157 606/88 |
| 5,667,511 A | 9/1997 | Vendrely et al. | |
| 5,704,941 A * | 1/1998 | Jacober | A61B 17/157 606/88 |
| 6,221,035 B1 | 4/2001 | Kana et al. | |
| 6,277,123 B1 | 8/2001 | Maroney et al. | |
| 10,792,049 B2 * | 10/2020 | Fiedler | A61B 17/1764 |
| 2005/0070910 A1 * | 3/2005 | Keene | A61B 17/157 606/88 |
| 2006/0189998 A1 | 8/2006 | Rasmussen | |
| 2006/0241639 A1 * | 10/2006 | Kuczynski | A61B 17/155 606/88 |
| 2008/0027471 A1 | 1/2008 | Hauri | |
| 2012/0053594 A1 * | 3/2012 | Pelletier | A61B 90/06 606/86 R |
| 2016/0367291 A1 | 12/2016 | Erickson et al. | |
| 2017/0245893 A1 | 8/2017 | Sanders et al. | |

FOREIGN PATENT DOCUMENTS

| | | |
|---|---|---|
| DE | 60212852 T2 | 8/2007 |
| DE | 102006035602 A1 | 2/2008 |
| DE | 202015101629 U1 | 7/2015 |
| GB | 2398010 A | 8/2004 |
| JP | 2008125706 A | 6/2008 |
| JP | 2011092405 A | 5/2011 |
| WO | 03013371 A1 | 2/2003 |
| WO | 2012027816 A1 | 3/2012 |
| WO | 2013134595 A1 | 9/2013 |

OTHER PUBLICATIONS

International Search Report received in International Application No. PCT/EP2019/082964 dated Mar. 6, 2020, with translation, 10 pages.

Search Report received in German Application No. 10 2018 130 117.0 dated Sep. 5, 2019, with translation, 14 pages.

Search Report received in German Application No. 10 2018 130 119.7 dated Sep. 5, 2019, with translation, 11 pages.

Written Opinion received in International Application No. PCT/EP2019/082960 dated Feb. 5, 2020, with translation, 13 pages.

Written Opinion received in International Application No. PCT/EP2019/082964 dated Mar. 6, 2020, with translation, 9 pages.

Office Action received in Japanese Application No. 2021-546788 dated Feb. 25, 2022, with translation, 10 pages.

Search Report received in German Application No. 10 2019 103 880.4 dated Oct. 23, 2019, with translation, 16 pages.

Search Report received in International Application No. PCT/EP2020/053740 dated Oct. 9, 2020, with translation, 5 pages.

Written Opinion received in International Application No. PCT/EP2020/053740 dated Oct. 9, 2020, with translation, 9 pages.

* cited by examiner

FIXING CLAMP AND ALIGNING DEVICE

CROSS REFERENCE TO RELATED APPLICATION(S)

This application is the United States entry of International Application No. PCT/EP2019/082960, filed Nov. 28, 2019, and claims the benefit of priority of German Application No. 10 2018 130 117.0, filed Nov. 28, 2018. The contents of International Application No. PCT/EP2019/082960 and German Application No. 10 2018 130 117.0 are incorporated by reference herein in their entireties.

FIELD

The present invention relates to a fixing clamp/fixing clip for an aligning device, in particular for a tibial resection, for fixingly clamping a body extremity of a patient, such as a tibia or malleolus of a tibia, an ankle, a leg, an ankle joint, comprising a first clamp arm and a second clamp arm and a frame device having an attaching portion for attachment to an adjustment rod and a first rotary joint and a second rotary joint to which the respective first and second clamp arms are rotatably attached about respective first and second axes of rotation. In addition, the invention relates to an aligning device/adjustment guide for a tibial resection guide.

BACKGROUND

Precise resection of a patient's bone, especially the tibia, is of great importance for the success of an operation to implant a joint prosthesis. The plane of the resection must be precisely localized here in order to minimize a degree of bone removal on the one hand, while at the same time ensuring that all of the defective bone tissue is also removed. The alignment of the plane in relation to an anatomical axis, in particular a tibial axis, has to be continuously monitored during surgery to ensure the alignment of the articular surfaces of the joint over the entire range of joint motion.

The exact definition of a tibial resection plane in a knee joint is usually set using an aligning device or an adjustment guide (for a saw block) with a columnar adjustment rod, which is fixed remote from the tibia close to the ankle. The adjustment rod extends along the tibia (substantially) parallel to the corresponding anatomical tibial axis. The resection plane can then be defined with respect to the tibial axis. Finally, a sawing block or guiding block (cutting block/guiding device) attached to the aligning device defines the plane of the resection. Typically, the guiding block has a passage gap through which a reciprocating, plane cutting edge of a surgical instrument (saw) is passed.

For adjusting the alignment of the tibial resection plane, a fixing clamp is attached near the patient's ankle, which is bound to the adjustment rod at its one end facing a patient's foot, and to whose other end (end portion) the saw/guide block is fixed/fixable.

In the prior art, various forms of an aligning device and an associated fixing clamp are disclosed.

For example, US 2016/0367291 A1 discloses an adjustment guide having two rod-shaped components, each of which has a ball joint at its end portions and is arranged substantially symmetrically with respect to the tibial axis on the left and right of the foot or leg. A fixing clamp in the form of a U-shaped frame with screws drilled into the heel bone fixes the two rod-shaped components. The adjustment guide has a plurality of adjustment possibilities for an alignment of a guiding block or guiding device. However, it is disadvantageous that bone substance is unnecessarily removed for fixation by screwing into the heel bone and healthy bone tissue is damaged. Also, the distal fixation cannot be subsequently changed and adjusted.

U.S. Pat. No. 6,221,035 B1 discloses a (fixation) clamp for an alignment aid used in a tibial resection. The clamp has two spring-loaded clamp arms, each of which can be rotated about an axis of rotation relative to a frame. These clamp arms are brought into an open position and, after contact with the tibia, are released by means of a manual release device. Due to the spring preload, they then enclose an ankle joint or the tibia and clamp it. The clamp arms are pretensioned in the closing direction. The spring preload causes a force-fit fixation, which has the disadvantage, however, that hematomas can occur on the patient's body due to the clamping force. It is also not possible to adjust the clamping force.

US 2017/0245893 A1 also discloses an aligning device and an associated fixation device. In one embodiment, a screw is drilled through the heel bone to fix a fixed point of the aligning device. CN 205379351 U also discloses an aligning device in which screws are screwed into foot bones for fixation.

U.S. Pat. No. 5,197,944 A discloses an orthopedic instrument and in particular an ankle clamp or fixing clamp that allows a surgeon to fix the ankle clamp to a patient with one hand as part of the tibial alignment assembly. In particular, this clamp has a locking feature that secures the movable arms of the clamp in an open position until the clamp is positioned for use, at which time the locking feature of the arms of the clamp can be released and the clamp is then firmly secured by pretension about the patient's ankle. The arms are thereby movable between an open position and a closed position, and are pretensioned with springs to assume the closed position which grips the patient's ankle during use. The arms have a notched end portion for this purpose, which is located near the pivot point of the arm. This notch works in conjunction with a latch to secure the arms in an open position. The latch has an external pressure plate surface that can be manually depressed to release the latch from the respective movable arm.

However, one problem of the prior art is that the fixation to the patient's ankle is either only force-fitted or the clamp arms are pretensioned by force fit but not held in position by form fit (which results in insufficient positionability due to the resulting inherent elasticity of the clamp arms), or that screws have to be screwed into a (healthy) bone for fixation (which additionally stresses the patient and also increases the risk of infection). This leads, in the case of the force-fit connection, to a detachable fixation, which is, however, insufficient due to the high requirements for dimensional accuracy or accuracy to the alignment of the plane of the resection described at the beginning, and leads, in the case of fixation by means of screws, to further damage to the bone, which is, however, not necessary and should be prevented. Furthermore, the clamping force of elastically prestressed clamping arms can cause hematomas on the patient's body parts. Furthermore, not all anatomical sizes are covered by the fixing clamps according to the state of the art, since the clamping force depends on the respective anatomy of the patient. Therefore, different variants of fixing clamps have to be manufactured and kept available.

SUMMARY

It is therefore the object of the invention to avoid or at least reduce the disadvantages of the prior art and, in particular, to provide a fixing clamp and an aligning device which permit simple, secure and fast fixation and simple and fast release of the fixation of a body extremity/limb, in particular at or around the ankle joint and the tibia, wherein the fixing clamp and the aligning device are adapted for different anatomies of body extremities, in particular of the ankle joint, and can be used for any anatomy and by their modes of operation and configurations prevent hematomas, and a clamping force of the fixing clamp can be adjusted in discrete steps.

The core of the present invention therefore consists in determining the movability of the clamping arms/clamping fingers as well as determining the clamping force to be generated by them not by their inherent flexibility, but in designing the clamping arms/clamping fingers (which are rigid/stable in shape compared to the state of the art) with a self-locking joint/hinge in each case, by means of which the degree of opening of the clamping arms/clamping fingers, which can be pivoted relative to one another, can be varied, and the clamping force can be maintained as a function of an actuating force applied to the clamping arms/clamping fingers in a targeted (metered) manner from the outside in the closing direction as a result of their self-locking effect, even if the external actuating force is removed. Advantageously, the self-locking effect of the joints/hinges against independent movement of the clamping arms in the opening direction is achieved by a (ratchet-like) manually-releasable latching mechanism, which is preferably arranged in the region of each joint/hinge and supports/latches the corresponding clamping arm/clamping finger in the opening direction relative to a base to which the clamping arms are hinged/attached.

Specifically, the object of the invention is solved in a generic fixing clamp according to the invention by a latching mechanism which form-fittingly latches a first clamping/clipping arm and/or a second clamping/clipping arm relative to a base, hereinafter referred to as frame device, in at least one position, preferably in a plurality of selectable pivot positions, and blocks a pivotal movement of the first or second clamp arm about the respective rotary joint in an opening rotation direction. The opening rotation direction is the direction of rotation in which the (tips of the) clamp arms (also referred to as clamping fingers) move away from each other, thus opening the fixing clamp. By means of the form fit and blocking of the opening rotation direction of the clamp arms, a user can discretely adjust the clamping or the geometric fixation of the clamping arms and thus ultimately the clamping force. A clamping spring is no longer required for a force-locking fixation, but the fixation is achieved/held positively by the latching mechanism. The user can therefore manually press the clamp arms together (in the closing rotation direction) and lock them in at least one position via the latching mechanism. When the clamp arms are attached around an ankle joint, they can, due to their geometry, for example, in cooperation with the elasticity of the body tissue, press slightly against the latter in order to achieve a tight fit. Hematoma formation, however, can be suppressed, since no spring pretension is applied, which would compress the clamp arms further in the closing rotation direction beyond an uncontrolled, possibly extensive clamping force. Furthermore, the user does not have to press the clamp arms apart again against the pretensioning force, but he/she can move the clamp arms back into their original position when the form closure is released in a certain way. This improves handling. It is also not necessary to ensure that the spring force always corresponds to a predetermined value and, in particular, does not lose its pretension over a period of time. This also simplifies or eliminates the need for maintenance.

In a preferred embodiment, the latching mechanism can be activated and deactivated. In order to release the fixing clamp, the clamp arms have to be released from the positive locking engagement. For this purpose, the latching mechanism can be deactivated, wherein an active engagement or a form fit is cancelled. Preferably, the latching mechanism can be activated and deactivated manually.

In particular, the latching mechanism is realized in the form of a ratchet mechanism. A ratchet mechanism with a ratchet wheel (gear wheel) and a (spring-preloaded) detent is a particularly suitable design in which a special geometric shape of the teeth allows a rotational movement in one direction and locks in the opposite rotational direction. The ratchet mechanism allows the fixing clamp to move in the closing rotation direction and locks the opposite movement in the opening rotation direction.

According to one aspect of the invention, the ratchet mechanism on the frame device may comprise one, preferably two, ratchet pawl(s) having a rocking axis of rotation parallel to the axis of rotation of the associated rotary joint associated with the first clamp arm and/or second clamp arm. The ratchet pawl is pretensioned in a tilting direction about the tilting axis of rotation to positively lock the opening rotation direction of the associated clamp arm, and the ratchet pawl is disengaged by a tilting movement about the tilting axis of rotation against the pretension so that the associated clamp arm is free to rotate about its axis of rotation and is not locked. Such a system is similar in function to a ratchet mechanism in which a detent is spring pretensioned and engages a ratchet wheel. The ratchet pawl additionally allows the user to manually release or unlock it. For this purpose, the ratchet pawl can be pressed and tilted against the pretension and the ratchet mechanism comes out of (form-fit) engagement and is thus deactivated. If the ratchet pawl is released again, it returns to its "normal state" of active engagement due to the pretension and the latching mechanism in the form of the ratchet mechanism is then activated again.

Preferably, the ratchet pawl may have a ramp structure or a latch hook on the side facing the associated clamp arm, and may have a recessed grip adapted to a finger and in particular ribbed, on the side facing away from the associated clamp arm in order to manually move the ratchet pawl against pretension. This indicates to the user an area to be pressed in order to deactivate the ratchet mechanism. The geometry of a recess, which can optionally be supplemented with ribbing, supports targeted and safe actuation.

According to a further preferred embodiment, the fixing clamp may comprise a locking mechanism that can lock/restrain/fix the ratchet pawl in a (tilting) position in which it is in operative engagement with the associated clamp arm and can block a tilting movement about the tilting axis of rotation so that unintentional unlocking and release of the clamp arms is prevented. Thus, the locking mechanism causes a (form-fit) operative engagement between the ratchet pawl and the associated clamp arm to remain in a locked state until the user explicitly changes the locking mechanism from the locked state to an unlocked state. Only then can the ratchet pawl be manually actuated, the operative engagement can be cancelled and the ratchet mechanism can be deactivated. Such a locking mechanism represents a safety mechanism to prevent, for example, the fixing clamp from being released unintentionally during an ongoing operation and resection and the previously defined resection plane from being lost.

In a preferred embodiment, the first clamp arm and/or the second clamp arm may be pretensioned in the opening rotation direction opposite to the closing rotation direction, in particular by a spring. In this way, the locking in the opening rotation direction of the latching mechanism and the pretension in the opening rotation direction cooperate optimally. If the (form-fit) locking is now removed by the latching mechanism, the clamp arm(s) is/are automatically moved back into its/their open position due to the pretension.

According to a further preferred embodiment, the frame device may be V-shaped or Y-shaped and comprise a frame base as well as a first frame branch and a second frame branch, wherein the first frame branch and the second frame branch are translationally movable on the frame base in a displacement direction relative thereto, so that alignment of the first and second frame branches relative to the attaching portion is adjustable. This provides the user with a further adjustment option of the fixation clamp relative to the adjustment rod in a transverse plane. The plane of the tibial resection can thus be rotated or inclined to a certain extent relative to the tibial axis.

In particular, the fixing clamp may be rotationally symmetrical with respect to an axis of symmetry between the first clamp arm and the second clamp arm, such that the fixing clamp has identical components on the side of the first clamp arm and on the side of the second clamp arm. In particular, the first clamp arm and the second clamp arm are an identical component, the first frame branch and the second frame branch are an identical component, and the first ratchet pawl and the second ratchet pawl of the latching mechanism in the form of a ratchet mechanism are an identical component. This creates a modular system with a very small number of necessary components and improves production and interchangeability.

In a preferred embodiment, the frame device may comprise at least one rotation device/rotation adjustment device for adjusting the position of the first frame branch and/or of the second frame branch relative to the frame base in the displacement direction. In particular, the rotation device comprises a setscrew/threaded spindle with external thread, which is axially fixedly attached to the first frame branch and the second frame branch and engages a block with internal thread on the frame base in order to adjust an alignment with respect to the frame base and thus the attaching portion and optionally a distance between the first frame branch and the second frame branch.

The object of the invention is achieved in a generic adjustment guide or alignment device for a tibial resection guide for use in preparing a knee joint for implantation of a prosthesis with an adjustment rod which can be aligned with a tibia of a patient, a guiding device at one end of the adjustment rod adapted to guide a tool during a resection or operation of the tibia, and a fixing clamp arranged at the other end of the adjustment rod or towards the other end of the adjustment rod, which engages around/embraces and fixes the tibia of the patient in order to fix the adjustment rod in relation to the tibia, is solved according to the invention by using a fixing clamp according to the invention. The aligning device can be quickly and easily aligned and arranged on a tibia or with respect to a tibia of the patient by means of the fixing clamp according to the invention, and can be released again just as easily in order to reposition or remove the aligning device. Handling is greatly simplified and hematomas are prevented.

BRIEF DESCRIPTION OF THE DRAWING FIGURES

The figures are merely schematic in nature and serve only for understanding the invention. Identical elements are provided with the same reference signs.

DETAILED DESCRIPTION

A preferred embodiment of the present invention is described below with reference to the accompanying figures.

Figure 1:
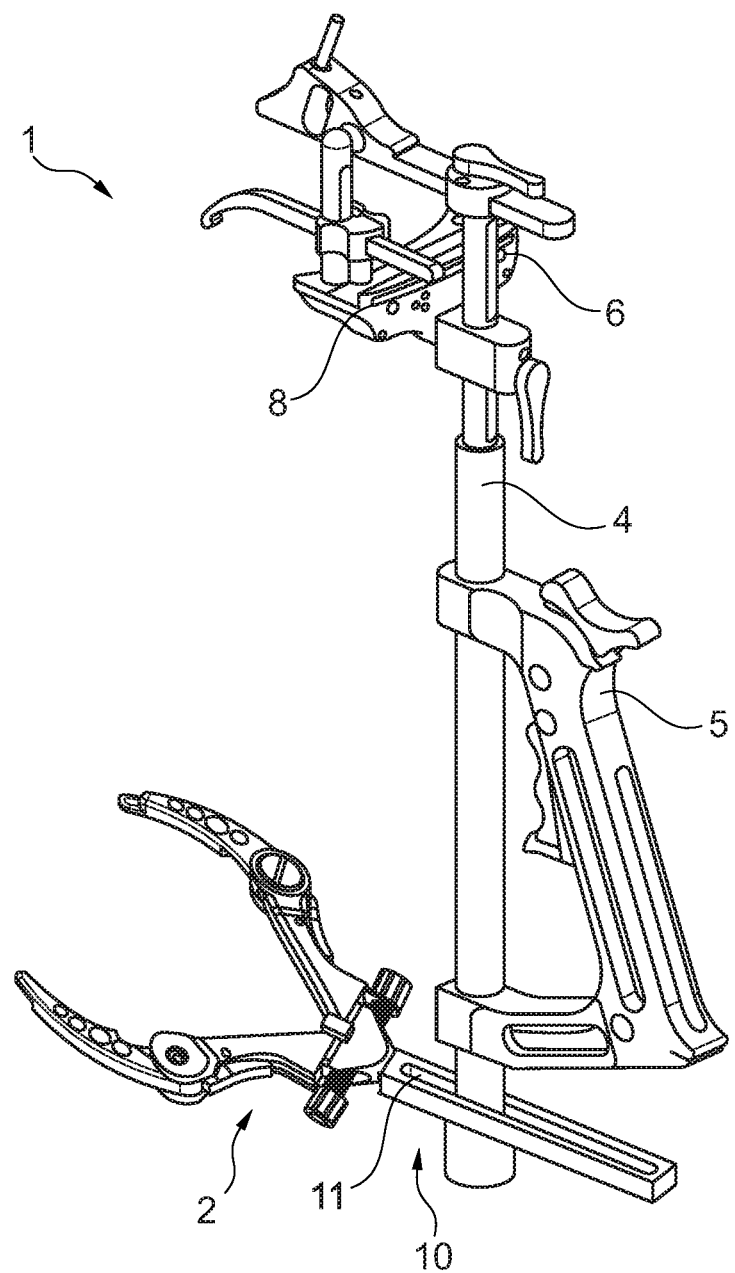
FIG. 1 shows a perspective view of an aligning device according to the invention according to a preferred embodiment.

FIG. 1 shows a perspective view of an aligning device 1 according to a preferred embodiment of the invention for a tibial resection guide for use in preparing a knee joint for implantation of a knee joint prosthesis with a fixing clamp 2 according to the invention of a preferred embodiment.

The aligning device 1 has a length-adjustable telescopic rod 4 as an adjustment rod with a handle 5 rigidly mounted thereon, so that the telescopic rod 4 can be aligned with respect to a tibia of a patient (not shown). At one end of the telescopic rod 4, which faces the patient's thigh when aligned with the patient, a (tool) guiding device 6 in the form of a (saw) block with a plane passage gap or passage opening through the block is attached as a cutting gap or guiding gap 8, through which a tool can be inserted or guided. The (plane) cutting gap 8 defines the plane of the resection. The fixing clamp 2 according to the invention is hinged or fastened at an end of the telescopic rod 4 opposite the guiding device 6, which is turned towards the foot when aligned with the patient. The fixing clamp 2, which is described in detail below with reference to FIGS. 2 and 3, serves to define a fixed point for the aligning device 1 and, for this purpose, grips/encompasses (in a clamping manner) an ankle of the patient.

The fixing clamp 2 has a block-shaped, elongated cantilever arm/cantilever 10 as an attaching portion for connection/fixing/assembly to the adjustment rod 4. The cantilever arm 10 has a passage opening along its longitudinal axis L in the form of a passage gap 11, wherein the end of the telescopic rod 4 facing the foot protrudes into or through the passage gap 11 and thereby preferably elastically presses apart the two clamps of the cantilever arm 10 formed by the longitudinal slit 11. Due to the geometric interaction, the fixing clamp 2 can be translationally displaced longitudinally with respect to the adjustment rod 4 in order to adjust a position in the sagittal plane or an offset between the fixing clamp 2 and the guiding device 8. Furthermore, the cantilever arm 10 can be equipped with an (additional) pretensioning device (symbolically shown at the free end of the cantilever arm), by means of which the clamping force of the two clamps of the cantilever arm 10 on the telescopic rod 4 clamped by them can be further increased.

As can be seen from FIG. 1, a number of handling means (actuating buttons/actuating wheels) can be provided on the handle 5, by means of which, for example, functions of the telescopic rod 4 or the position adjustment of the handle 5 on the telescopic rod 4 can be actuated.

Figure 2:
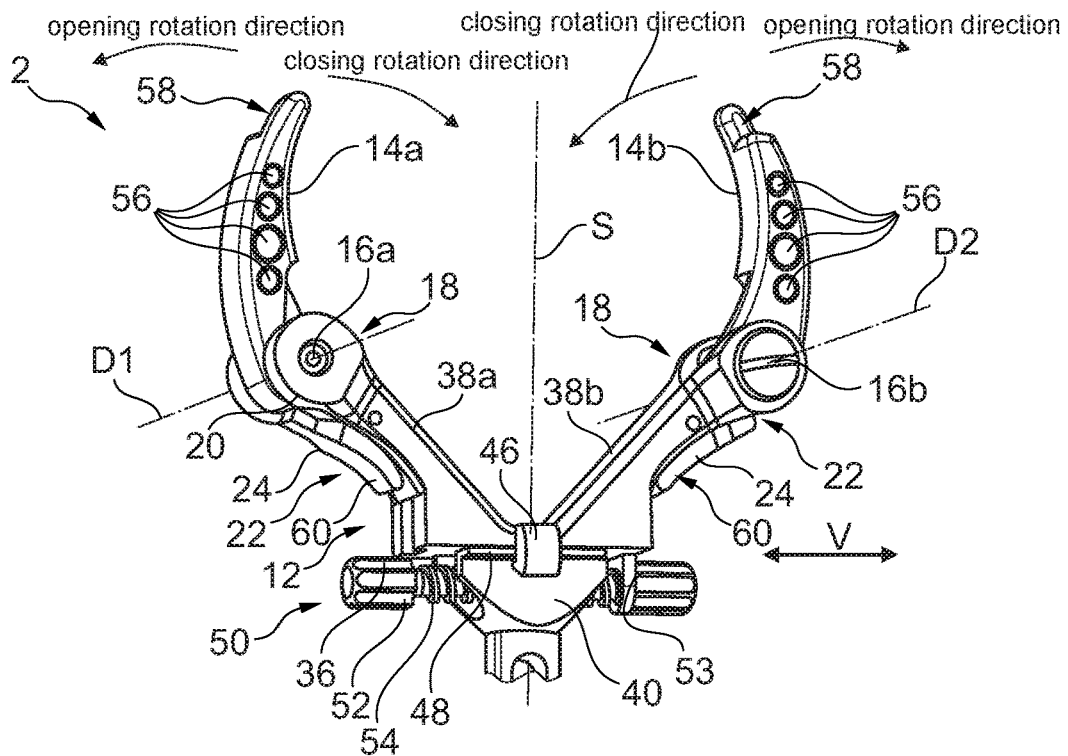
FIG. 2 shows a perspective view of a fixing clamp according to the invention in accordance with a preferred embodiment.
Figure 3:
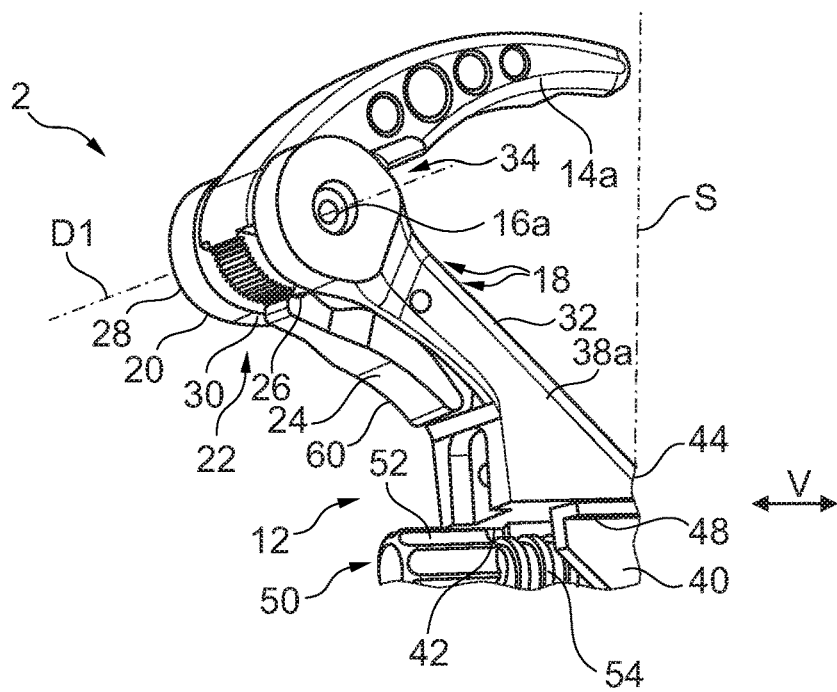
FIG. 3 shows an enlarged, partial perspective view of the fixing clamp of FIG. 2.

FIGS. 2 and 3 show a perspective view and partial perspective view, respectively, of the fixing clamp 2 according to the invention.

The fixing clamp 2 has a (rigid) base frame device 12 in the form of a Y (Y-shaped fork), wherein the fixing clamp 2 is rotationally symmetrical about an axis of symmetry S. In other words, the frame device 12 is formed as a kind of a bearing recess/bearing fork for the body extremity. A first (rigid) clamp arm (clamping finger) 14a and a second (rigid) clamp arm (clamping finger) 14b are rotatably attached or hinged to a first rotary joint 16a about a first axis of rotation D1 and to a second rotary joint 16b about a second axis of rotation D2, respectively, at both end portions 18 of the Y-shaped frame device 12 spaced from the symmetrical plane S. These end portions 18 of the frame device 12 are each fork/groove-shaped when viewed from the side, or have a gap/recess/groove between two flat, parallel (inner) surfaces of the end portions 18 when viewed in the direction of the axis of rotation D1, D2, so that the associated clamp arm 14a, 14b is enclosed between the fork-shaped end portions 18 in the manner of a hinge. A hinge pin 20, which has an external thread for axially fixed positioning on a (short) end portion, which is screwed into an internal thread as a mating thread of the frame device 12, holds the clamping arms 14a, 14b in position and enables a rotary movement about the respective axis of rotation D1, D2.

In FIG. 2, the fixing clamp 2 is shown in an (opened) state in which the clamp arms 14a, 14b are open and the fixing clamp 2 can be arranged in particular on the malleolus of the tibia of a patient in order to grip/encompass it later. FIG. 3 shows in contrast a state of the fixing clamp 2 in which the clamp arms 14a, 14b have been rotated about the respective rotary joints 16a, 16b further in a closing rotation direction (see arrows), i.e. towards the symmetrical plane S, about the axis of rotation D1, D2. In this state, the two clamp arms 14a, 14b geometrically grip/embrace the malleolus of the tibia and clamp the tibia and the ankle joint, respectively. In this (closed/fixed) state, the fixing clamp 2 is firmly arranged opposite the tibia and thus the tibial axis and defines a fixed point for the aligning device 1 (see FIG. 1).

In order to hold the clamp arms 14a, 14b in the respective (rotational) position relative to the frame device 12 or to fix/lock them in the opening direction, the fixing clamp 2 has a self-locking/holding mechanism, preferably a form-fitting latching mechanism, in particular in the form of a ratchet mechanism 22, although it is pointed out at this point that the holding mechanism can also be a friction-locking mechanism. In the particular embodiment shown, two ratchet mechanisms 22 are provided for the first clamp arm 14a and the second clamp arm 14b, respectively. The ratchet mechanism 22 form-fittingly engages respectively the first clamp arm 14a and the second clamp arm 14b in a selectable plurality of (rotational) positions in the closing rotational direction and locks the respective clamp arm 14a, 14b in the opening rotational direction, as will be explained below.

The ratchet mechanism 22 has a ratchet pawl 24 for form-fitting latching, which is received in the frame device 12 so as to be pivotable about a tilting axis of rotation. The tilting axis of rotation is preferably parallel to the axis of rotation D1, D2 of the associated rotary joint 16a, 16b. The ratchet pawl 24 and the clamp arms 14a, 14b further preferably lie in a common plane orthogonal to the direction of the axis of rotation D1, D2 and have no height difference or offset from each other in the direction of the axis of rotation D1, D2. The side of the ratchet pawl 24 facing the clamp arm 14a, 14b has a latching structure/detent preferably in the form of a ramp structure 26 or latch hook having three sawtooth shaped protrusions with asymmetrical tooth flanks. The latching structure, in particular in the form of this ramp structure 26, engages, when the ratchet pawl 24 is resiliently pressed against the associated clamp arm 14a, 14b, for example, and rests there, in a complementary latching structure in the form of an arm-ramp structure 28 of the clamp arms 14a, 14b, which form the ratchet wheel associated with the detent.

In other words, each clamp arm 14a, 14b forms an external toothing in the area of the respective rotary joint, in which the ratchet pawl 24 engages in a form-fitting manner at its latching structure (ledge/edge) and thus permits rotation of the respective clamp arm 14a, 14b in the closing direction, but blocks counter-rotation of the clamp arm 14a, 14b in the opening direction.

The combination of the ramp structure 26 and the arm-ramp structure 28 thus makes it possible to block rotation in one direction of rotation, namely the opening rotation direction, and together forms a latch. On the one hand, this allows the ramp structure 26 and the arm-ramp structure 28 to slide on each other in the closing rotation direction and, on the other hand, prevents a rotational movement in the opening rotation direction, similar to the latching mechanism of a handcuff, in particular due to the asymmetrical tooth flank structure with undercuts in the form of planar rear surfaces 30 of the arm-ramp structure 28, which in the operative engagement lies substantially parallel to a complementary tooth flank of the ramp structure 26 and presses against the latter.

The ratchet pawl 24 is preloaded against the respective clamp arm 14a, 14b by a (spiral or leaf) spring 32, so that the ratchet pawl 24 is in operative engagement/form fit with the associated clamp arm 14a, 14b or its arm-ramp structure 28 and is thus always activated in the normal, manually unactuated state. Only when the ratchet pawl 24 is manually moved about the tilting axis of rotation against the pretension of the spring 32, do the ramp structure 26 and the arm-ramp structure 28 become disengaged, is the positive engagement released and is the ratchet mechanism 22 deactivated. Thereafter, the clamp arm 14a, 14b associated with the ratchet mechanism 22 can be freely rotated or pivoted about its axis of rotation D1, D2. Geometric stops in the frame device 12 cause a limitation of the rotational movement or pivoting movement of the clamp arms 14a, 14b both in the closing rotation direction and in the opening rotation direction, so that a range of a pivoting angle of about 90° is defined in each case.

In order to automatically open the clamp arms 14a, 14b when the ratchet pawl 24 is actuated against pretension, the fixing clamp 2 has a return spring 34 in the form of a coil spring on each clamp arm 14a, 14b which pretensions the clamp arms 14a, 14b in the opening rotation direction.

Thus, with reference to the method of operation, the fixing clamp 2 according to the invention can be applied or arranged by a user in an open state on a tibia of the patient. The user can then press the clamp arms 14a, 14b (manually) inwards in a measured manner in the closing rotation direction, whereby the ratchet mechanism 22 engages tooth by tooth of the arm-ramp structure 28 in accordance with a freewheel and blocks the opening rotation direction, so that as a result the clamp arms 14a, 14b lie firmly against the tibia or the malleolus of the patient's tibia and clamp this. If the user now wishes to release the fixing clamp 2 from the patient's leg, the user presses on a side of the ratchet pawl opposite the ramp structure 26 so that the ramp structure 26 and the arm-ramp structure 28 disengage and the associated clamp arm 14a, 14b automatically rotates in the opening rotation direction due to the pretension of the return spring 34. The user can then either push the clamp arms 14a, 14b inwards again, for example to set a lower clamping force than before, or he can release the fixing clamp 2 from the patient's leg and reposition it or remove it completely.

A clamping force of the fixing clamp 2 can be discretely adjusted by the number of teeth of the arm-ramp structure 28. In contrast to the prior art, the fixing clamp 2 according to the invention provides the user with a selectable clamping force or fixing force, which he can adapt to the patient accordingly. For example, a large and possibly overweight person will require a higher clamping force than a small, petite person. The clamp arms 14a, 14b always remain in the selected position due to the ratchet mechanism 24 in interaction with the return spring 34.

In the embodiment shown in FIGS. 2 and 3, the frame device 12 is configured in two parts with a V-shaped frame fork 36 having a first frame branch 38a and a second frame branch 38b, and a frame base 40. The frame fork 36 has a planar sliding surface 42 on the side facing the attaching portion 10, which can slide translationally in a displacement direction V on a planar sliding surface 44 of the frame base 40. In order to be connected to the frame base 40 so that it can only move axially in displacement direction V, the frame fork 36 has two L-shaped guiding hooks/encompassing means 46, each of which, similar to a guiding rail, surrounds a guide bar 48 or guide projection of the frame base 40.

The frame base 40 further comprises a fulcrum shaft 50 for rotational adjustment. A rotatable setscrew/or threaded spindle 52 with external thread 54 engages an (adapter) block with internal thread mounted on the frame base 40. The setscrew 52 further protrudes through a borehole of a web 53 and is axially fixed to the frame fork 36 by the latter, so that a rotation of the setscrew 52, corresponding to the pitch of the external thread 54, causes a translational displacement of the block and thus of the frame fork 36 in the displacement direction V. This allows the alignment of the frame fork 36 to the frame base 40, and thus to the cantilever arm 10, to be adjusted. Thus, the fixing clamp 2 of the aligning device 1 can cause, among other things, an adjustment of the inclination of the guiding device 6 and thus of the guiding gap 8 or of the resection plane.

In this preferred embodiment, the frame fork 36 is made in one piece. Alternatively, however, it is also possible for the frame fork to be designed in two parts with the first frame branch as the first component and the second frame branch as the second component, so that the two frame branches can be positioned individually with respect to the frame base, each with their own guiding hooks/encompassing means and their own rotation devices. In this way, the distance between the first frame branch and the second frame branch can also be adjusted, which enables improved adaptation to the patient's anatomy.

In this embodiment, the fixing clamp 2 is configured rotationally symmetrical with respect to the axis of symmetry S. That is, the first frame branch 38a and the second frame branch 38b are identical components which are rigidly fixed to each other centrally, in the present embodiment welded, and thus form the frame fork 36; the first clamp arm 14a and the second clamp arm 14b are identical components; the two hinge pine 20 are identical components and the ratchet pawls 24 are identical components. The frame base 40 is also formed rotationally symmetrical to the axis of symmetry S, except for the web 53. This provides an efficient modular system in which a small number of different components leads to improved production.

The clamp arms 14a, 14b have, located along their longitudinal axis, four passage openings 56 or through holes of different diameters whose axes are parallel to the axis of rotation D1, D2. These passage openings 56 serve to receive further components. The tips of the clamp arms 14a, 14b each have a complementary recess/cutout 58 in a direction parallel to the axes of rotation D1, D2, so that in the closed state the clamp arms 14a, 14b not only contact each other at the end faces, but even overlap each other due to the recess 58. Thus, they form an annular, gapless fixing clamp 2. It can also be said that the tips of the clamp arms 14a, 14b have a step or offset in a direction parallel to the axes of rotation D1, D2.

For actuation, the ratchet pawl 24 has a grooved grip recess 60 for a finger, so that the user also presses in the correct place and does not slip off. In particular, the grip recess is ribbed to achieve a better grip.

Alternatively, or in addition to the embodiment described above, instead of or in addition to the spring, a spiral spring may be arranged around the tilting axis of rotation of the ratchet pawl 24 itself, which realizes a pretension of the ratchet pawl 24. Alternatively, the ratchet pawl can also be designed as a single piece with the frame device and can be designed to be movable about a virtual tilting axis of rotation via an elastic section (not shown).

In a further variant (not shown), in an end position of the clamp arms desired by the user, a further rotational movement in the closing rotation direction can be blocked, for example by a pin which fixes the ratchet pawl, so that unintentional further closing of the clamp arms is prevented and the clamp arms are completely fixed.

In this embodiment, the clamp arm 14a, 14b respectively has the passage openings 56 which, in addition to having the function described above, also geometrically increase elasticity of the clamp arm 14a, 14b. Although the present invention is described above with reference to the preferred embodiment, it will be understood that various embodiments and modifications may be implemented. In particular, the elasticity of a clamp arm can be adjusted by structural design of the clamp arm as is common to the person skilled in the art, such as by means of webs, notches, material recesses, struts, and/or by a particular choice of material of the clamp arm (material having elastic or rigid properties). In particular, the clamp arm can also have different sections of different materials with correspondingly different elasticity, for example in order to incorporate defined elasticity sections.

The invention claimed is:

1. A fixing clamp for an aligning device for fixingly clamping a body extremity, the fixing clamp comprising:
    a first clamp arm and a second clamp arm;
    a frame device forming a bearing recess or bearing fork for the body extremity, the frame device having a central mounting or attaching portion for mounting or attaching to an adjustment rod of the aligning device and having a first rotary joint and a second rotary joint at two bearing fork ends of the frame device, to which the first clamp arm is articulated rotatably about a first axis of rotation and the second clamp arm is articulated rotatably about a second axis of rotation; and
    a self-locking mechanism comprising two latching mechanisms that frictionally and/or form-fittingly hold or latch the first clamp arm and the second clamp arm relative to the frame device in at least one position independent from each other and thereby block a movement of the first clamp arm and the second clamp arm about the first rotary joint and the second rotary joint, respectively, in an opening rotation direction without applying a spring pretension in a closing rotation direction, wherein the frame device is V-shaped or Y-shaped and has a frame base and a first frame branch and a second frame branch, and the first frame branch and the second frame branch are adapted to be translationally displaced on the frame base in a displacement direction to set an alignment with respect to the central mounting or attaching portion.

2. The fixing clamp according to claim 1, wherein the latching mechanisms are adapted to be individually activated and deactivated.

3. The fixing clamp according to claim 1, wherein the latching mechanisms are each in the form of a ratchet mechanism.

4. The fixing clamp according to claim 3, wherein the ratchet mechanisms comprise a first ratchet mechanism and a second ratchet mechanism, wherein the first ratchet mechanism comprises a first ratchet pawl having a tilting rotation axis parallel to the first axis of rotation and the second ratchet mechanism comprises a second ratchet pawl having a tilting rotation axis parallel to the second axis of rotation, wherein the first ratchet pawl and the second ratchet pawl are each pretensioned in a tilting direction in order to form-fittingly lock the opening rotation direction of the first clamp arm and second clamp arm, respectively, and the first and second ratchet pawls are each disengaged by a tilting movement against pretension so that the first and second clamp arms are free to rotate about the first and second axis of rotation, respectively.

5. The fixing clamp according to claim 4, wherein each of the first ratchet pawl and the second ratchet pawl has a ramp structure or a latch hook on a side facing the first clamp arm and second clamp arm, respectively, and has a grip recess adapted to a finger on a side facing away from the first clamp arm and second clamp arm, respectively, in order to move the first ratchet pawl and second ratchet pawl manually against pretension.

6. The fixing clamp according to claim 5, wherein each of the first ratchet pawl and the second ratchet pawl is in the form of a seesaw having the ramp structure or the latch hook on a first side of the seesaw facing the respective clamp arm, and having the grip recess on a second side opposite the first side and facing towards a lateral side of the bearing recess or bearing fork.

7. The fixing clamp according to claim 1, wherein the first clamp arm and/or the second clamp arm is pretensioned in the opening rotation direction opposite to a closing rotation direction.

8. The fixing clamp according to claim 1, wherein the fixing clamp is configured to be rotationally symmetrical with respect to an axis of symmetry between the first clamp arm and the second clamp arm, so that the fixing clamp has identical components on a side of the first clamp arm and on a side of the second clamp arm.

9. The fixing clamp according to claim 1, wherein the frame device has a rotation device with which a position of the first frame branch and of the second frame branch relative to the frame base is adjustable in the displacement direction.

10. An aligning device for a tibial resection guide, the aligning device comprising:
a fixing clamp according to claim 1;
an adjustment rod which is adapted to be aligned with respect to the tibia of the patient; and
a guiding device at a first end of the adjustment rod adapted to guide a tool during a resection of the tibia of the patient, wherein
the fixing clamp is arranged at a second end of the adjustment rod opposite the first end, and
the fixing clamp is configured to grip and fix the tibia of the patient in order to fix the adjustment rod in relation to the tibia of the patient.

11. The fixing clamp according to claim 1, wherein the latching mechanisms are adapted to form-fittingly hold or latch the first clamp arm and the second clamp arm relative to the frame device in a plurality of predefined positions between a maximum open position and a maximum closed position.

12. The fixing clamp according to claim 1, wherein the two latching mechanisms block said movement of the first clamp arm and the second clamp arm about the first rotary joint and the second rotary joint, respectively, in the opening rotation direction while permitting free movement of the first clamp arm and the second clamp arm about the first rotary joint and the second rotary joint, respectively, in a closing rotation direction.

13. A fixing clamp for an aligning device for fixingly clamping a body extremity, the fixing clamp comprising:
a first clamp arm and a second clamp arm;
a frame device forming a bearing recess or bearing fork for the body extremity, the frame device having a central mounting or attaching portion for mounting or attachment to an adjustment rod of the aligning device and having a first rotary joint and a second rotary joint at two bearing fork ends of the frame device, to which the first clamp arm is articulated rotatably about a first axis of rotation and the second clamp arm is articulated rotatably about a second axis of rotation; and
a self-locking mechanism comprising a latching mechanism that frictionally and/or form-fittingly holds or latches the first clamp arm and/or the second clamp arm relative to the frame device in at least one position and blocks a movement of the first clamp arm and/or the second clamp arm about the first rotary joint and/or the second rotary joint, respectively, in an opening rotation direction without applying a spring pretension in a closing rotation direction.

14. The fixing clamp according to claim 13, wherein the self-locking mechanism comprises two latching mechanisms, and wherein the two latching mechanisms are adapted to be individually activated and deactivated independently from each other.

15. The fixing clamp according to claim 13, wherein the latching mechanism is in the form of a ratchet mechanism.

16. The fixing clamp according to claim 15, wherein the ratchet mechanism comprises a ratchet pawl having a tilting rotation axis parallel to the first axis of rotation and/or the second axis of rotation, wherein the ratchet pawl is pretensioned in a tilting direction in order to form-fittingly lock the opening rotation direction of the first clamp arm and/or second clamp arm, and the ratchet pawl is disengaged by a tilting movement against the pretension so that the first clamp arm and/or second clamp arm is free to rotate about the first axis of rotation and/or second axis of rotation, respectively.

17. The fixing clamp according to claim 16, wherein the ratchet pawl has a ramp structure or a latch hook on a side facing the associated clamp arm and has a grip recess adapted to a finger on a side facing away from the associated clamp arm in order to move the ratchet pawl manually against pretension.

18. A fixing clamp for an aligning device for fixingly clamping a body extremity, the fixing clamp comprising:
a first clamp arm and a second clamp arm;
a frame device forming a bearing recess or bearing fork for the body extremity, the frame device having a central mounting or attaching portion for mounting or attachment to an adjustment rod of the aligning device and having a first rotary joint and a second rotary joint at two bearing fork ends of the frame device, to which in each case the corresponding first clamp arm is articulated rotatably about a first axis of rotation and the second clamp arm is articulated rotatably about a second axis of rotation; and
a self-locking mechanism comprising a latching mechanism that frictionally and/or form-fittingly holds or latches the first clamp arm and/or the second clamp arm relative to the frame device in at least one position and blocks a movement of the first and/or second clamp arm about the first and/or second rotary joint, respectively, in an opening rotation direction, wherein the first clamp arm and/or the second clamp arm is pretensioned in the opening rotation direction opposite to a closing rotation direction, wherein the latching mechanism has a first asymmetrical tooth flank structure at the first clamp arm and/or the second clamp arm, the first asymmetrical tooth flank structure having undercuts comprising planar rear surfaces of a first ramp structure, which in a locking state, lies substantially parallel to a complementary tooth flank of a second asymmetrical tooth flank structure of a second ramp structure.

19. The fixing clamp according to claim 18, wherein the self-locking mechanism comprises two latching mechanisms, and wherein the two latching mechanisms are adapted to be individually activated and deactivated independently from each other.

20. The fixing clamp according to claim 18, wherein the latching mechanism is in the form of a ratchet mechanism.

21. The fixing clamp according to claim 20, wherein the ratchet mechanism comprises a ratchet pawl having a tilting rotation axis parallel to the first and/or second axis of rotation, wherein the ratchet pawl is pretensioned in a tilting direction in order to form-fittingly lock the opening rotation direction of the associated clamp arm, and the ratchet pawl is disengaged by a tilting movement against pretension so that the associated clamp arm is free to rotate about its axis of rotation.

22. The fixing clamp according to claim 21, wherein the ratchet pawl has a ramp structure or a latch hook on a side facing the associated clamp arm and has a grip recess adapted to a finger on a side facing away from the associated clamp arm in order to move the ratchet pawl manually against pretension.

23. The fixing clamp according to claim 18, wherein the latching mechanism is adapted to form-fittingly hold or latch the first clamp arm and the second clamp arm relative to the frame device in a plurality of predefined positions between a maximum open position and a maximum closed position.

* * * * *